United States Patent [19]

Fernstrom et al.

[11] 4,298,611

[45] Nov. 3, 1981

[54] PROCESS FOR REDUCING BLOOD PRESSURE IN ANIMALS

[75] Inventors: John D. Fernstrom, Boston; Alan F. Sved, Brighton, both of Mass.

[73] Assignee: Massachusetts Institute of Technology, Cambridge, Mass.

[21] Appl. No.: 898,741

[22] Filed: Apr. 24, 1978

[51] Int. Cl.³ ............................................. A61K 31/48
[52] U.S. Cl. .................................. 424/261; 424/256; 424/319
[58] Field of Search ........................ 424/261, 256, 319

[56] References Cited

U.S. PATENT DOCUMENTS 4,054,660 10/1977 Clemens et al. ..................... 424/261

OTHER PUBLICATIONS

Chemical Abstracts 73:118899k (1970).
Chemical Abstracts 74:38823m (1971).
Chemical Abstracts 81:99933p (1974).

Primary Examiner—Leonard Schenkman
Attorney, Agent, or Firm—Arthur A Smith, Jr.; Paul J. Cook

[57] ABSTRACT

Blood pressure in animals is reduced by administering 2-chloro-6-methylergoline-8β-acetonitrile (lergotrile*) or pharmaceutically acceptable salts thereof either alone or in combination with a substance which is known to reduce blood pressure. A novel composition is provided comprising a unit dosage form of lergotrile and a substance which is known to reduce blood pressure.

(* The term "lergotrile" is intended to include the compound lergotrile as well as its physiologically- and pharmacologically-active metabolites in the body.)

2 Claims, No Drawings

PROCESS FOR REDUCING BLOOD PRESSURE IN ANIMALS

BACKGROUND OF THE INVENTION

This invention relates to a method and composition for reducing blood pressure in animals.

At the present time, the most widely used medicaments for lowering blood pressure such as α-methyl dopa (Aldomet), 11,17α-dimethoxy-18β-[(3,4,5-trimethoxybenzoyl)oxy]-3β,20α-yohimban-16β-carboxylic acid methyl ester (Reserpine) or 2-(2,6-dichlorophenylamino) 2-imidazoline hydrochloride (Clonidine hydrochloride) also stimulate the secretion of prolactin in humans. This side effect is potentially objectionable, inasmuch as in recent years, a category of breast carcinoma has been described that is enhanced in its development by high circulating levels of prolactin. It has been shown in experimental animals that Reserpine which is used commonly to treat hypertension and release prolactin also increases the incidences of breast cancer.

Accordingly, it would be highly desirable to provide an otherwise innocuous means for reducing hypertension in animals which could serve either as a substitute for or an adjunct to present means for reducing hypertensions in order to eliminate or substantially reduce the problems of increased prolactin secretion which accompany the administration of presently available drugs.

SUMMARY OF THE INVENTION

The present invention is based upon the discovery that the compound, 2-chloro-6-methylergoline-8β-acetonitrile (lergotrile) or pharmaceutically acceptable salts thereof reduces hypertension when administered to animals without effecting increased secretion of prolactin. The compound is admixed with an innocuous vehicle which does not degrade the compound and the mixture can be administered intraperitonally, subcutaneously, intramuscularly or orally.

DESCRIPTION OF SPECIFIC EMBODIMENTS

The compound 2-chloro-6-methylergoline-8β-acetonitrile (lergotrile) or its pharmaceutically acceptable salts are available from Eli Lilly and Company, Indianapolis, Ind. Prior to the present invention, lergotrile has been administered to humans to suppress the secretion of prolactin by the pituitary gland, and to patients suffering from Parkinson's disease, to attempt to reduce involuntary tremor. It is surprising that lergotrile also reduces blood pressure since it is a known agent for reducing serum prolactin levels; the commonly used blood pressure reducing agents effect increased secretion of serum prolactin levels.

While the mechanism by which lergotrile produces reduced blood pressure had not yet been determined, it is believed that the mechanism may be different than that of Aldomet, Clonidine hydrochloride or Reserpine since it actually reduces prolactin secretion rather than increasing it. In addition, unlike Aldomet, lergotrile reduces blood pressure in animals having normal blood pressure.

The administration of the compositions employed in the present invention can be effected orally, intraperitonally, subcutaneously, intraveneously or intramuscularly. Conveniently,, the compositions employed in this invention are admixed or dissolved in any innocuous vehicle such as water or sterile saline solution or in tablet or powder form containing the usual solid diluents or carriers. When producing a lowering of blood pressure, the compositions employed in the present invention are administered in concentrations to avoid undesirable side effects. The compound, lergotrile, is employed in dosages sufficient to effect lowering of blood pressure while minimizing the possibility of producing undesirable side effects such as orthostatic hypotension. In humans, useful dosages are between about 0.01 mg/kg and 1 mg/kg, preferably between about 0.1 mg/kg and 0.5 mg/kg. Dosages below about 0.01 mg/kg body weight do not produce significant lowering of blood pressure while concentrations above about 1.0 mg/kg body weight do not product significant additional lowering of blood pressure and may produce undesirable side effects. When utilizing this invention, lowering of blood pressure is produced for about 4.5 hours.

In another aspect of this invention, it has been found that the co-administration of lergotrile and a compound selected from the group consisting of Aldomet, Reserpine and Clonidine or their pharmaceutically acceptable salts which dissociate in vivo to produce one of these compounds produces an additive effect of lowering blood pressure. In order to obtain this additive effect, useful concentrations of lergotrile are between about 0.01 and 0.5 mg/kg body weight compounded with the main antihypertensive agent. In these compositions, Reserpine is employed in amounts between about 0.007 and 0.0035 mg/kg, Aldomet in amounts between about 1.5 mg/kg and 30 mg/kg and Clonidine in amounts between about 0.0014 mg/kg and 0.035 mg/kg.

The following examples illustrate the present invention and are not intended to limit the same.

EXAMPLE I

This example illustrates that lergotrile alone produces a lowering blood pressure in animals having either normal or high blood pressure.

Male SHR (Spontaneously Hypertensive Rats), rats of the Okamoto Strain, and normotensive Sprague-Dawley rats (Charles River Breeding Laboratories) weighing between 350 and 450 grams were used in these experiments. The animals were housed in pairs and given ad libitum access to food and water. Blood pressures were determined using the tail vein plethysmography technique: Rats were warmed at b 38° C. for 15 minutes prior to each measurement to dilate the tail vessels. The tail cuff then was placed around the tail with the pressure sensor attached. Eight readings were taken rapidly for each timepoint studied. The pressure monitoring system utilized was a Narco Biosystems Pneumatic Pulse Transducer. All animals used in the studies had their blood pressures taken several times, on separate days, to acclimate them to the procedure and thus minimize falsely high blood pressures due to the stress of an unfamiliar procedure. Experiments were performed in the morning or early afternoon. Lergotrile mesylate in varying amounts was injected intraperitoneally in a water solution and control animals received water alone. Blood pressure measurements were made prior to and after drug administration. At each timepoint, the animals were warmed and then eight successive pressure readings were taken rapidly for each animal. In the dose-response experiments, blood pressures were taken one hour after drug administration, as well as shortly before drug injection. One hour post injection was determined to be the timepoint at which the maximal lowering effect was observed. The results are shown in Tables I, II and III.

TABLE I
BLOOD PRESSURE LOWERING IN NORMOTENSIVE RATS

| Lergotrile Dosage, mg/kg | Blood Pressure Change, mm Hg 1 Hour after Administration |
|---|---|
| 0 | — |
| 0.1 | −11.2 |
| 0.5 | −16.2 |
| 1.0 | −28.7 |

TABLE II
BLOOD PRESSURE LOWERING IN SHR RATS

| Lergotrile Dosage, mg/kg | Blood Pressure Change, mm Hg 1 Hour after Administration |
|---|---|
| 0 | — |
| 0.05 | −28 |
| 0.1 | −42 |
| 0.25 | −65.5 |
| 0.5 | −70.5 |
| 1.0 | −76 |

TABLE III

| Time after Lergotrile Administration | Blood Pressure Change, mm Hg |
|---|---|
| 0 | 0 |
| 1.5 | −57 |
| 3.0 | −30 |
| 4.5 | −12 |

Dose employed: 0.5 mg/kg

EXAMPLE II

This example shows that the administration of Aldomet and lergotrile has an additive effect in lowering blood pressure.

The procedures for measuring blood pressures herein are set forth in Example I. Male SHR rats were used in this experiment. Blood pressures were taken just prior to administration. In a first administrative step, lergotrile (0.1 mg/kg) or water (as controls) was administered to the rats. Blood pressures were taken 1 hour later. Aldomet (50 mg/kg) then was administered to both groups. Blood pressures then were taken 1.5 hours after the Aldomet was administered. The results are shown in Table IV.

TABLE IV

| Time | Water & Aldomet Blood Pressure, mm Hg | Lergotrile & Aldomet Blood Pressure, mm Hg |
|---|---|---|
| −1 hr | 212 | 206 |
| 0 | 210 | 157 |
| +1.5 hr | 176 | 131 |

As shown in Table IV, lergotrile by itself had a significant lowering effect on blood pressure. The administration of Aldomet had a significant effect of lowering blood pressure in both groups of animals. Thus, lergotrile does not block the action of Aldomet in reducing blood pressure. Furthermore, this Aldomet and lergotrile treatment has the desirable effect of lowering serum prolactin levels. Experiments conducted by administering lergotrile and Aldomet simultaneously also show the additive blood pressure lowering effect:

TABLE V

| Time | Aldomet (25 mg/kg) Blood Pressure, mm Hg | Aldomet (25 mg/kg) Lergotrile (0.1 mg/kg) Blood Pressure, mm Hg |
|---|---|---|
| 0 | — | — |
| 1.5 | −25 | −56 |
| 3.0 | −38 | −77 |
| 4.5 | −29 | −27 |

We claim:
1. The process for reducing blood pressure in an animal suffering from high blood pressure which comprises administering a compound selected from the group consisting of 2-chloro-6-methylergoline-8Beta-acetonitrile, a pharmaceutically acceptable salt of 2-chloro-6-methylergoline-8Beta-acetonitrile, and mixtures thereof to the animal in an amount effective to reduce blood pressure.
2. The process of claim 1 wherein the animal is a human.

* * * * *